(12) United States Patent
Wolf et al.

(10) Patent No.: US 11,097,884 B2
(45) Date of Patent: Aug. 24, 2021

(54) PACKAGING AND PROCESS FOR THE STERILE PACKAGING OF OBJECTS FOR MEDICAL, PHARMACEUTICAL OR COSMETIC APPLICATIONS

(71) Applicant: SCHOTT AG, Mainz (DE)

(72) Inventors: Patrick Wolf, St. Gallen (CH); Gregor Fritz Deutschle, Idstein (DE); Volker Rupertus, Alzey (DE)

(73) Assignee: SCHOTT AG, Mainz (DE)

( * ) Notice: Subject to any disclaimer, the term of this patent is extended or adjusted under 35 U.S.C. 154(b) by 52 days.

(21) Appl. No.: 16/731,644

(22) Filed: Dec. 31, 2019

(65) Prior Publication Data

US 2020/0407142 A1    Dec. 31, 2020

(30) Foreign Application Priority Data

Jun. 27, 2019  (EP) .................................... 19183002

(51) Int. Cl.

| | | |
|---|---|---|
| *B65D 77/00* | (2006.01) |
| *B23B 7/12* | (2006.01) |
| *B32B 27/08* | (2006.01) |
| *B32B 27/32* | (2006.01) |
| *B32B 27/34* | (2006.01) |
| *B32B 27/36* | (2006.01) |
| *B65D 65/40* | (2006.01) |

(Continued)

(52) U.S. Cl.
CPC .............. *B65D 77/003* (2013.01); *B32B 7/12* (2013.01); *B32B 27/08* (2013.01); *B32B 27/32* (2013.01); *B32B 27/34* (2013.01); *B32B 27/36* (2013.01); *B65D 65/40* (2013.01); *B65D 77/26* (2013.01); *B32B 2307/72* (2013.01); *B32B 2439/46* (2013.01)

(58) Field of Classification Search
CPC ...... B65D 77/003; B65D 65/40; B65D 77/26; B32B 7/12; B32B 27/08; B32B 27/32; B32B 27/34; B32B 27/36; B32B 2307/72; B32B 2439/46
See application file for complete search history.

(56) References Cited

U.S. PATENT DOCUMENTS

2006/0016708 A1    1/2006  Ingraham
2017/0203534 A1*   7/2017  Lahti ..................... B32B 7/06

FOREIGN PATENT DOCUMENTS

| EP | 0269324 | 6/1988 |
| EP | 0307173 | 3/1989 |

* cited by examiner

*Primary Examiner* — Michael C Miggins
(74) *Attorney, Agent, or Firm* — Ohlandt, Greeley, Ruggiero & Perle, L.L.P.

(57) ABSTRACT

Packaging for the sterile storage and transport of objects for medical, pharmaceutical or cosmetic applications and a packaging process are provided. The packaging includes at least one bag made of a first and a second web, bonded to one another, a feature thereof being that the first web consists of a selectively permeable nonwoven fabric and that the second web consists of a laminated film with at least three layers, where the first layer is a polymer film arranged on the external side of the bag, the second layer is a lamination adhesive and the third layer is a polymer film arranged on the internal side of the bag. At least one of the layers of the second web includes one or more pigments. In an 8-bit greyscale image, the seal seam, imaged in transmitted light and contrast-standardized, is depicted within a greyscale value range of 50-200.

17 Claims, 3 Drawing Sheets

(51) Int. Cl.
*B65D 77/26* (2006.01)
*B32B 7/12* (2006.01)

PACKAGING AND PROCESS FOR THE STERILE PACKAGING OF OBJECTS FOR MEDICAL, PHARMACEUTICAL OR COSMETIC APPLICATIONS

CROSS REFERENCE TO RELATED APPLICATIONS

This application claims benefit under 35 USC § 119 of European Application 19183002.5 filed Jun. 27, 2019, the entire contents of which are incorporated herein by reference.

BACKGROUND

1. Field of the Invention

The present invention relates to packaging for the sterile storage and transport of objects for medical, pharmaceutical or cosmetic applications, in particular of sterile primary pharmaceutical packaging means, for example vials, ampoules, syringes or carpules, and a packaging process.

2. Description of Related Art

Primary pharmaceutical packaging means, for example vials, ampoules, syringes and carpules, are generally packaged under sterile conditions in what are known as tubs and trays by the manufacturers before delivery to the pharmaceutical industry for filling. These tubs mostly consist of a support, which holds a large number of the primary packaging means and is known as the nest, and of a trough or shell into which the support is inserted. In the case of trays, a large number of the primary packaging means are inserted directly into the tray. The tubs and trays here are usually protectively covered by a microfibre nonwoven fabric produced by the flash-spinning process, made of high-density polyethylene (HDPE) and known by the trade mark Tyvek® of DuPont. Because the Tyvek® nonwoven is selectively permeable, it is also possible to use ethylene oxide or steam to sterilize the space within the tub or within the tray after the said space has been protectively covered, with simultaneous creation of a microbial barrier. Prior to sterilization, the tubs and trays are generally enclosed securely within one or two bags.

The pharmaceutical industry uses controlled, sterile conditions for removal of the packaging from the sterile primary packaging means and filling of the same. Procedures known as disinfection steps are carried out here on transition from higher to lower cleanroom classes. These can involve the removal of a packaging layer, e.g. of a bag, or else biological decontamination inter alia by means of electron beam, hydrogen peroxide or wiping with an alcohol solution. Before the tubs or trays are transferred into the aseptic region where the Tyvek® sealant film is removed and then the active pharmaceutical ingredient is charged to the primary packaging means, there is initially also a further decontamination step. This is necessary because it is not possible to ensure the sterility of the external side of the tub or of the tray.

The definition of bags generally requires that—irrespective of the fill aperture—at least one of the three sides has not been sealed, welded or adhesive-bonded, i.e. that it is a lateral-seam bag or a basal-seam bag, produced from a tube or from a halved tube or a folded flat film. In contrast to this, pouches are generally defined as having a welded seam or seal seam or adhesive bond at all three sides, because they are produced from two or more separate film webs. The closed pouch accordingly then has a welded bond, sealed bond or adhesive bond at all sides. For the purposes of this application, the term "bag" is employed as an umbrella term applying not only to bags but also to pouches.

A reason for the impossibility of ensuring the sterility of bag packaging consists in the extent to which the seal seams are impermeable and durable. Various defects can arise in the seal seam not only during sealing of bags during production but also during the final sealing of the bag after filling; these result from what is known as undersealing or oversealing, i.e. sealing outside of ideal parameters. In the case of undersealing, the layers are insufficiently bonded because temperatures, pressures or sealing times are inadequate, and the resultant seal seam therefore exhibits low adhesion. The defect is apparent in seal-seam separation or in formation of channels and cavities.

In contrast to the above, oversealing results in small holes termed pinholes in the seal seam, caused by excessive temperatures, pressures or sealing times; the polymer, melting in its entirety, is laterally displaced, and the remaining seal seam is therefore too thin, and moreover can also suffer further thinning in the region where it adjoins the remainder of the film; or in extreme cases the polymer actually suffers thermal degradation.

There is insufficient possibility for checking of the seal seams while the production process is running, because the defects are not sufficiently discernible during conventional inspection of the seal seams from the film side by camera. Crystalline Tyvek® nonwovens melt in the region of the seal seam during sealing and thus lose their white colour at those locations; the resultant poor contrast makes it very difficult to discern the transparent seal seam and defects therein by optical methods.

SUMMARY

The present invention is intended to eliminate these disadvantages of the prior art. In particular, a packaging is to be provided that ensures the sterility of the contents in a manner that is reliable and can be guaranteed, thus eliminating the previous requirement for an additional sterilization step carried out by the pharmaceutical industry.

In another aspect, the intention is to permit improved detection of seal seam defects.

This object is achieved via packaging for the sterile packaging of objects for medical, pharmaceutical or cosmetic applications comprising at least one bag made of a first and a second web, bonded to one another, a feature thereof being that the first web consists of a selectively permeable nonwoven fabric and that the second web consists of a laminated film with at least three layers, where the first layer is a polymer film arranged on the external side of the bag, the second layer is a lamination adhesive and the third layer is a polymer film arranged on the internal side of the bag; at least one of the layers of the second web comprises one or more pigments.

In one embodiment, the melting point of the polymer of the first layer is above the sealing-initiation temperature of the third layer by at least 20° C.

For the purposes of this application, the expression "melting point of the polymer" means the peak minimum of the melting peak of the second heating cycle in differential scanning calorimetry (DSC) with heating rate 20 K/min. For the purposes of this application, the expression "sealing-initiation temperature of the polymer" means the temperature at which a seal seam strength of at least 4 N/15 mm, measured in accordance with DIN EN 868-5:2009 Annex D, is achieved during the sealing of the two webs of the bag.

In an 8-bit greyscale image recorded in transmitted light and contrast-standardized, the seal seam in one embodiment is depicted within a greyscale value range of 50-200.

For the purposes of the application, the term "contrast-standardized" means a linear expansion of the greyscale-value scale of the recorded image to the full 0-255 range of the 8-bit scale, so that contrast is maximized. If $g_{min}$ and $g_{max}$ define the minimal and maximal greyscale values of the image, the expanded greyscale-value scale is calculated from the following formula:

$$f(g) = \frac{255}{g_{max} - g_{min}} \cdot (g - g_{min})$$

In one embodiment, the remission $\tau_{vis}$ of the seal seam, measured in accordance with DIN 5033-1:2009-5 in remission mode with 2° observer, is 10%-40%. The remission $\tau_{vis}$ can also be 12%-38%, 14%-36%, 16%-34%, 18%-32%, 20%-30%, 22%-28% or 24%-26%.

In one embodiment, the remission T, measured in remission mode with 2° observer in accordance with DIN 5033-1:2009-5, of the seal seam and of the first web exhibit a difference of 30-75 percentage points. The difference can also be 35-70, 40-65, 45-60 or 50-55 percentage points.

In an 8-bit greyscale image recorded in transmitted light and contrast-standardized, the seal seam in one embodiment exhibits greyscale values which are at least 30 units above, 40 units above, 50 units above, 60 units above, 70 units above, 80 units above, 90 units above or 100 units above the greyscale values of the region surrounding the seal seam.

It is preferable that in the second web the first layer is a polyester film or polyamide film and the third layer is a film made of polyethylene homo- or copolymers, of polypropylene homo- or copolymers or of polyester homo- or copolymers.

This structure of the bag achieves a plurality of advantages simultaneously. The design of the second web as laminated film reduces the risk of undesired permeability due to pinholes, which can arise during extrusion of the individual films. The lamination adhesive layer applied between the film layers seals any pinholes that may be present, thus eliminating leakages in the film.

An external layer of polyester or of polyamide improves the edge regions of the seal seam, in particular when heat is introduced from the polyester side or polyamide side. To this end, the melting point of the external first film layer can be above the sealing-initiation temperature of the internal third layer by at least 20° C., at least 25° C., at least 30° C., at least 35° C. or at least 40° C. The melting point of the first film layer can by way of example be at least 200° C., at least 210° C. or at least 220° C. The external layer therefore does not melt concomitantly during sealing; the only layer that melts is the interior layer functioning as sealable layer. The boundary area between the seal seam and the unsealed region of the nonwoven fabric is thus substantially less stressed than, for example, when the conventional simple film layer made of HDPE is used and is sealed to a Tyvek® nonwoven. This results in less failure of the Tyvek® layer or nonwoven fabric layer at the seal seam. The nonwoven fabric layer can moreover be fully melted throughout the seal seam; this leads to improved bonding of the layers, with increased seal seam strength, and also to a transparent or translucent seam, and by virtue of the laminated bond to the polyester layer or polyamide layer it is also possible to achieve increased puncture resistance of the film side of the bag.

Finally, the colouring of one or more of the film layers improves contrast and thus permits fully satisfactory detection not only of undersealing but also of oversealing. Because the seal seam is transparent or translucent, a camera can be used to study the seal in transmitted light. The seal seam is then particularly clearly visible when the increased contrast is combined with a camera directed onto the white nonwoven-fabric side of the packaging. It is thus possible, in a greyscale analysis of the transmitted-light image, to achieve reliable detection of every type of defect in the seal seam, and to isolate the bag. The only remaining restriction on the minimal detectable defect size is then the resolution of the camera system.

The quantity, particle size and colour of the pigments to be used here are to be selected according to the invention such that they optimize the appearance of the seal seam for optical detection of the seal seam and defects therein, in transmitted light or reflected light. To this end, adjustment of the quantity, particle size and colour of the pigments is preferably such that in a contrast-standardized 8-bit greyscale image the seal seam is depicted in a greyscale range of 50-200, 60-190, 70-180, 80-170, 90-160, 100-150 or 110-140. The greyscale values are preferably <200, <190, <180, <170, <160, <150. By this means it is possible to achieve particularly good contrast in relation to the surrounding area of the unsealed nonwoven layer.

It is moreover in particular also possible by way of quantity and particle size of the pigments to set a remission $\tau_{vis}$ of 10%-40%, 12%-38%, 14%-36%, 16%-34%, 18%-32%, 20%-30%, 22%-28% or 24%-26%, measured in remission mode with 2° observer in accordance with DIN 5033-1:2009-5 for the seal seam. With the resultant haze value of the seam, in conjunction with the increased contrast, it is possible to achieve particularly effective detection in the images of individual sealing defects. Variations in degrees of mattness in the seam indicate inhomogeneous melting or incorrect pressure applied by the sealing elements. Formation of microchannels in the seal seam can likewise be discerned very successfully, because these are clearly distinguishable from the surrounding matt area.

It can also be advantageous, on top of using only the pigments to establish the remission $\tau_{vis}$ measured in remission mode, to make additional use of a scattering additive which increases the proportion of back-scattered light, and thus increases the remission $\tau_{vis}$ measured in remission mode, without reducing remission to the same extent. The quantity of light remaining for the transmitted-light image after passage through the seal seam is thus increased, and this in turn can lead to improved contrast. These scattering additives, which can also themselves be coloured materials, are known in principle to the person skilled in the art by way of example from EP 0 269 324 A2. The scattering additive here can be used in the same layer(s) as the pigment, or can be used separately therefrom.

It is preferable that the polyester film or polyamide film of the first layer of the second web is free from pigments. This has the advantage of particularly effective detection of oversealing. Under ideal sealing conditions, no concomitant melting of the transparent or translucent polyester or polyamide layer occurs. When, in the case of oversealing, the coloured layers of the polyethylene and/or of the lamination adhesive situated thereunder are displaced, the camera image in transmitted light reveals transparent regions on each side of a coloured region within the otherwise white nonwoven fabric.

The selectively permeable nonwoven fabric of the first web can be a microfibre nonwoven fabric made of high-density polyethylene (HDPE), polypropylene (PP) or polyethylene terephthalate (PET). By way of example, the HDPE nonwoven fabrics of the Tyvek® range from DuPont are suitable for the purposes of the invention. It is preferable to use the uncoated products of the said range (e.g. Tyvek® 1073B). The ability of a nonwoven fabric to form a sterilizable microbial barrier, i.e. selective permeability in respect of barrier action for microbes with simultaneous permeability to sterilization media such as ethylene oxide or hydrogen peroxide vapours is an essential precondition for its selection.

The polymer of the third layer of the second web can be a polyethylene, polypropylene or polyester. The polymers here can be used in the form of homopolymers or in the form of copolymers composed of more than 50% of the specified monomers. It is preferable that the polymer here is selected appropriately for the polymer of the nonwoven fabric, in order to optimize sealability. Possibilities here are use of the same polymer class or indeed use of the same polymer type.

The polyethylene of the third layer of the second web can be a high-density polyethylene (HDPE), medium-density polyethylene (MDPE), low-density polyethylene (LDPE) or linear low-density polyethylene (LLDPE), or respective copolymers of these composed of more than 50% of the specified monomers. Preference is given to HDPE, MDPE or LDPE. HDPE has the advantage that the packaging can then also be sterilized with steam, in addition to ethylene oxide or hydrogen peroxide vapours. Sterilization by radiation is possible in all variants.

The polyester film of the first layer of the second web can consist of polyethylene terephthalate (PET) or polybutylene terephthalate (PBT). The polyamide film of the first layer of the second web can consist of PA 6, PA 6.6 or PA 12. Use of these materials ensures in each case that the bag has good puncture resistance together with good transparency. They thus contribute in two respects to the desired aim of packaging with sterility that can be guaranteed. Firstly, across the entire surface of the packaging they prevent undesired permeability due to defects or film failure under mechanical stress, and secondly they contribute to improvement of defect detection in the seal seams of the packaging.

The lamination adhesive of the second layer of the second web is preferably a polyurethane-based (PUR) adhesive. In particular, this adhesive is preferably a non-reactive PUR hotmelt adhesive. Pinholes are avoided throughout the entire film firstly simply through the lamination of the two films. Any pinholes that may be present in the individual films are additionally particularly effectively sealed by the PUR-based lamination adhesive. The quantity applied of the lamination adhesive can be 0.5-15 g/m$^2$ or 1.0-12 g/m$^2$ or 1.2-10 g/m$^2$ or 1.4-8.0 g/m$^2$ or 1.6-6.0 g/m$^2$ or 1.8-5.0 g/m$^2$ or 2.0-4.0 g/m$^2$.

In embodiments of the invention, the bonding of the webs of the bag, to form the bag, is achieved via sealing or adhesive bonding, and closure of the filled bag is achieved by means of a seal seam. It is preferable that seal seams are used not only to form the bag but also to close the filled bag. This permits checking of the integrity of the seams with the aid of a camera in transmitted light on all sides of the bag. The seal seam is moreover more robust than an adhesive bond.

The seal seam strength of the seal seams of the bag is most preferably at least 20 N/15 mm, at least 22 N/15 mm, at least 25 N/15 mm or at least 30 N/15 mm measured in accordance with DIN EN 868-5:2009 Annex D.

The puncture resistance measured in accordance with DIN EN 14477:2004 at test velocity 100 mm/min and with 0.8 mm tip diameter of the first web of the bag is preferably at least 10 N, at least 11 N, at least 12 N, at least 13 N or at least 14 N.

The puncture resistance of the second web of the bag, measured in accordance with DIN EN 14477:2004 at test velocity 100 mm/min and with 0.8 mm tip diameter, is preferably at least 4.5 N, at least 5.0 N, at least 5.5 N, at least 6.0 N or at least 6.5 N.

In one embodiment of the invention, arranged within the bag, there is a tub in the form of a trough or shell to receive the objects. Arranged in the tub there is preferably a support, known as a nest. The nest has optionally been securely bonded to the tub, preferably in a one-piece structure. In another embodiment of the invention, there is, arranged within the bag, a tray to receive the objects. A large number of primary pharmaceutical packaging means, for example vials, carpules or syringes, are thus frequently received, and securely arranged, either in the nest or in the tray.

The tub or tray has most preferably been protectively covered with a selectively permeable nonwoven fabric via sealing or adhesive bonding. This can be the same as the nonwoven fabric used to form the bag. However, it is also possible to use a different nonwoven fabric which has the same properties in respect of selective permeability but by way of example consists of a material better suited to sealing to the material of the tub or tray.

In another embodiment of the invention, the bag has been surrounded by one or more further bags. It is preferable here that the bags have the same structure as the first bag and merely have appropriately larger dimensions. The entire packaging thus created is suitable, in the steps of a packaging-removal procedure in a progressively cleaner environment, for avoiding contamination while bringing the contents to the usage location or filling location in the pharmaceutical industry. In those locations, in the case of packaging made of a sealed tub or tray surrounded by two bags, the first bag is accordingly opened in a class C cleanroom environment, the second bag is opened in class B, and finally the tub or tray is opened in class A.

A process of the invention for the sterile packaging of objects for medical, pharmaceutical or cosmetic applications features use of a packaging described above.

The invention moreover provides a process for seal seam monitoring for a bag made of a first web made of a selectively permeable nonwoven fabric and of, bonded thereto, a second web consisting of a laminated film with at least three layers, where the first layer is a polymer film arranged on the external side of the bag, the second layer is a lamination adhesive and the third layer is a polymer film arranged on the internal side of the bag, the melting point of the polymer of the first layer being above the sealing-initiation temperature of the third layer by at least 20° C., and where at least one of the layers of the second web comprises one or more pigments, comprising the steps of: provision of the webs of the bag in a manner such that in an 8-bit greyscale image recorded in transmitted light and contrast-standardized, the seal seam is depicted within a greyscale value range of 50-200, and the remission $\tau_{vis}$ of the seal seam, measured in accordance with DIN 5033-1:2009-5 in remission mode with 2° observer, is 10%-40%; imaging of the seal seam by a camera system in transmitted light to generate an 8-bit greyscale image, and contrast-standardization of the same; and evaluation of the contrast-standardized 8-bit greyscale image in respect of inhomogeneities in the greyscale values of the seal seam.

The packaging system of the invention is therefore successful in establishing optical monitoring—simply with the naked eye, or else in automated form with the aid of a camera inspection system—which permits reliable recognition of sealing defects not only in the case of oversealing but also in the case of undersealing. It is thus possible to isolate all bags with defects in the seal seam. The possible optimization of the seal seam moreover provides not only transparency or translucency thereof, which improves detection, but also improves seal seam strength.

DETAILED DESCRIPTION

Figure 1:
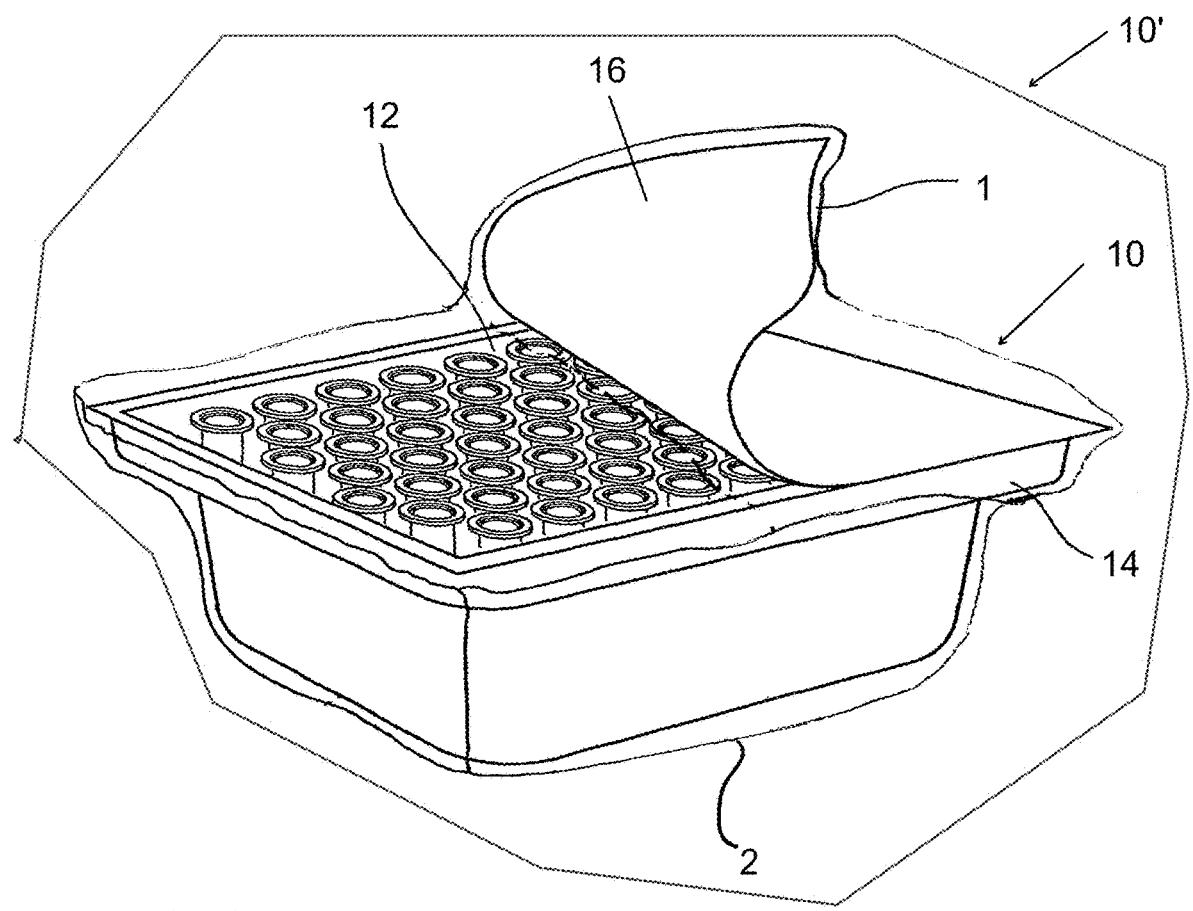
FIG. 1 shows an exemplary embodiment of a bag.

FIG. 1 illustrates an exemplary embodiment of a package or bag (10) of the present application that has a first web (1) and a second web (2) for sterile objects for medical, pharmaceutical or cosmetic applications (12). The sterile objects (12) can be, for example, sterile primary pharmaceutical packaging means, including vials, ampoules, syringes or carpules. In the illustrated embodiment, arranged within the bag (10), there is a tray (14) to receive the objects (12). A large number of primary pharmaceutical packaging means (12), for example vials, carpules or syringes, are thus frequently received, and securely arranged, either in the tray (14).

Figure 2:
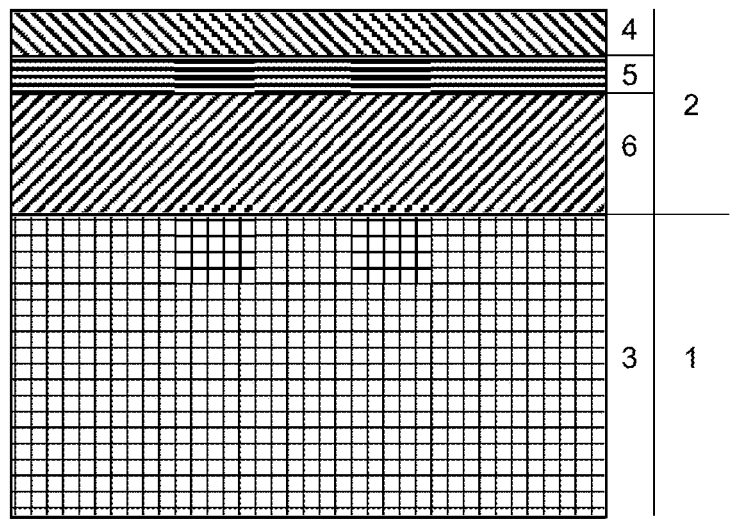
FIG. 2 shows the layer structure of a bag of Example 1.
Figure 3:
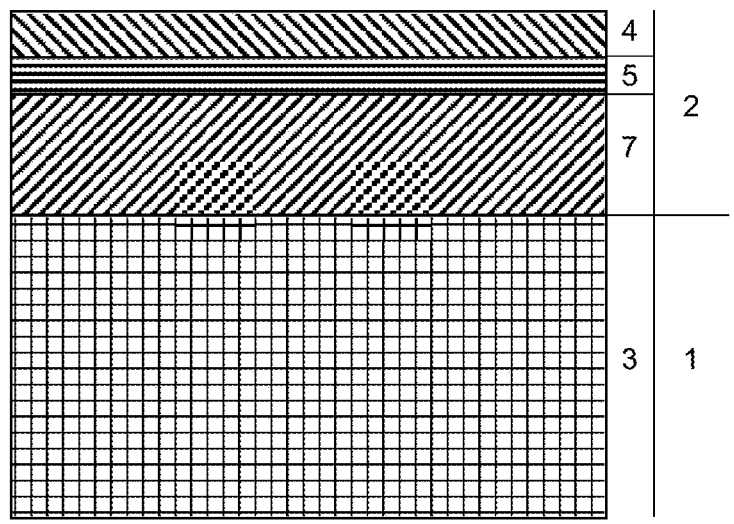
FIG. 3 shows the layer structure of a bag of Example 2.

FIGS. 2 and 3 illustrate a seal region of the first web (1) and the second web (2) to one another. The depiction of the layer thicknesses in FIGS. 2 and 3 is not to scale, but is merely a rough approximation.

The invention is described below on the basis of Examples. These serve merely to illustrate examples of embodiments of the invention, and are not to be understood as restrictive.

Example 1

Bags (10) were produced from a first web (1) and a second web (2). The first web (1) consisted of Tyvek® 1073 B uncoated nonwoven HDPE fabric (3) from DuPont with thickness about 180 μm. The second web (2) consisted of, arranged on the external side, a first layer (4) made of a PET film of thickness 12 μm and, bonded thereto by means of the second layer (5) of 2.5 g/m² of a PUR-based hotmelt lamination adhesive, a third layer (6) made of LDPE with thickness 50 μm. The third layer (6) made of LDPE had been coloured blue with a pigment, while the other two layers were transparent and colourless. The layer structure is depicted in FIG. 2.

Figure 4:
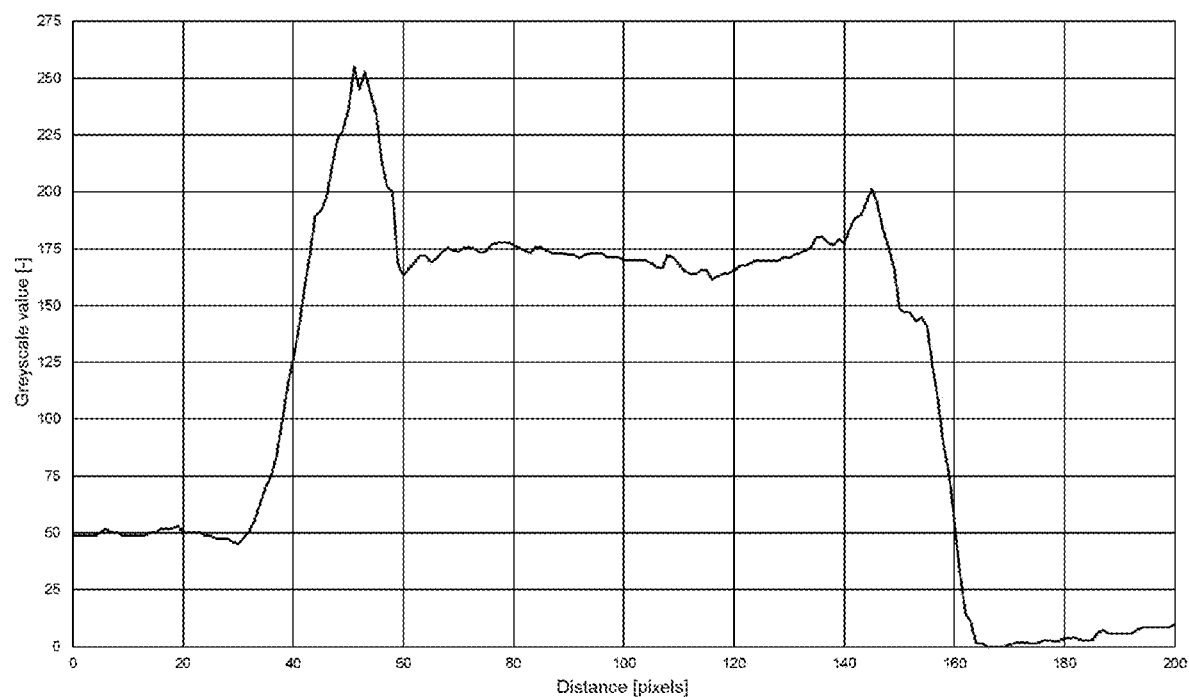
FIG. 4 shows an evaluation profile of a poor seal seam of Example 1.
Figure 5:
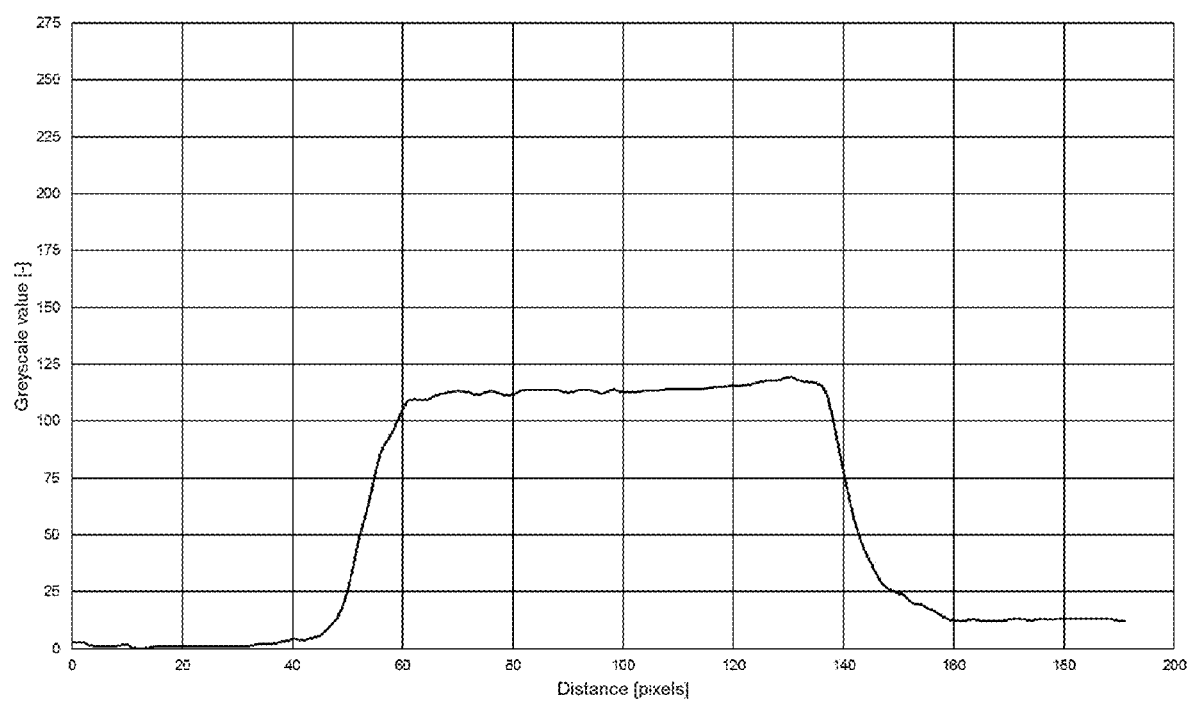
FIG. 5 shows an evaluation profile of a good seal seam of Example 1.

The bag (10) was formed by using an AccuSeal 6300-25-X impulse sealer at 180-190° C. with pressure 5.5-6 bar and sealing time 3-4 s to apply three seal seams of width 3 mm, 6 mm or 10 mm. Heat was introduced from one side: the polyester film side. A further seal seam was provided for the closure of the filled bag (10), thus then giving a packaging sealed at all sides. In the seal seam achieved during the sealing procedure, the molten nonwoven fabric layer was transparent, and the blue colour of the LDPE layer was clearly discernible. The seal seams were subjected to inspection by camera; cameras recorded images of the seal seams in transmitted light, and the images were then analysed. To this end, evaluation software was used in the standardized greyscale depictions to plot profiles at right angles across the seal seams. Each of FIGS. 4 and 5 shows by way of example an individual sectional profile through the seal seam. The greyscale value across the studied section is plotted here. For assessment at the seal seam in the production process, it will be self-evident that the software evaluates the depiction of the entire seal seam.

FIG. 4 depicts a defective seam. The transparent areas at the seam edges are clearly visible, revealed by pale peaks. Incorrect temperature and/or incorrect sealing jaw pressure here has caused the coloured LDPE sealable layer to disappear completely as a result of melting, so that the edges are then formed only by the transparent colourless PET film; these then appear in the white region of greyscale values in transmitted light.

In contrast to the above, FIG. 5 shows a fully satisfactory seal seam, the curve profile of which is very close to the ideal rectangular curve.

Example 2

Bags were produced from a first web (1) and a second web (2). The first web (1) consisted of Tyvek® 1073 B uncoated nonwoven HDPE fabric (3) from DuPont with thickness about 180 The second web (2) consisted of, arranged on the external side, a first layer (4) made of a PET film of thickness 12 μm and, bonded thereto by means of the second layer (5) of 2.5 g/m² of a PUR-based hotmelt lamination adhesive, a third layer (7) made of HDPE with thickness 50 μm. The third layer (7) made of HDPE had been coloured blue with a pigment, while the other two layers were transparent and colourless. The layer structure is depicted in FIG. 3.

The bag (10) was formed by using an AccuSeal 6300-25-X impulse sealer at 180-185° C. with pressure 5.7-6.2 bar and sealing time 3.5-4.5 s to apply three seal seams of width 3 mm, 6 mm or 10 mm. Heat was introduced from one side: the polyester film side. A further seal seam was provided for the closure of the filled bag (10), thus then giving a packaging sealed at all sides. In the seal seam achieved during the sealing procedure, the molten nonwoven fabric layer was transparent, and the blue colour of the HDPE layer was clearly discernible. As in Example 1, the seal seams were subjected to inspection by camera; cameras recorded images of the seal seams in transmitted light, and the images were then analysed. Here again, the seal seams were extremely easy to detect, and defects could be discerned in a fully satisfactory manner.

Test Methods

Seal seam strength was determined in accordance with DIN EN 868-5:2009-09. Five strips of width 15 mm and length 5 cm were cut out from the packaging material to be tested. The specimen here was cut out at right angles to the seal seam. The strips were moreover cut out at various positions along the seam to be tested, but with a minimum distance of 2 cm from the external edge. A mark was then made parallel to the seal seam on each strip at a distance of 3 cm from the seal seam towards the interior of the packaging. These marks served for clamping purposes. The entirety of the lower end of the strip was clamped into the lower clamp. The seal seam was parallel to the edge of the upper clamp. The other end of the test sample was clamped into the upper clamp in a manner such that the added markings were directly in contact with the lower edge of the upper clamp while the test sample had not yet been subjected to any stress. The test was then carried out with unsupported tab with test velocity 200 mm/min until failure of the test sample was observed.

Puncture resistance was determined in accordance with DIN EN 14477:2004. All samples were stored for at least 48 h at 23° C./50% rh. These were then tested under the same temperature/humidity conditions. The test included ten individual measurements per sample. The films were clamped into the tester with the internal side facing upwards. The test probe, diameter 0.8 mm, was forced through the film at a test velocity of 100 mm/min until failure occurred.

Remission $\tau_{vis}$, measured in remission mode with 2° observer in accordance with DIN 5033-1:2009-5, was measured with a Lambda 900 spectrometer from Perkin Elmer, which was used in remission mode and recorded in the range from 360 nm to 780 nm, equipped with a 60 mm integration sphere and with a sample holder at 11°. A standard D65 illuminant was used. Evaluation with 2° observer was carried out in accordance with DIN 5033-1:2009-5.

Seal Seam Strength

Sample strips of seal seams were taken as described above for seal seam strength measurement from all sides of the bags (10) formed. The measured values given in TABLE 1 are in each case the smallest values measured.

The resultant sample strips were tested as described above. A bag (10) in the usual embodiment using a web of DuPont Tyvek® 1073B (130-180 µm) and with a web of HDPE (80 µm) was taken as Comparative Example. TABLE 1 lists the test results.

TABLE 1

| Sample | Seal seam strength [N/15 mm] |
| --- | --- |
| Example 1 | 30 N |
| Example 2 | 27 N |
| Comparative Example | 12.5 N |

For the bags (10) of the invention with a laminate web, the measured values reveal on average a seal seam strength that is about two to three times greater than for the familiar variant with Tyvek® 1073B and HDPE.

Puncture Resistance

Samples of the two webs (1, 2) were taken for the bags (10) of Examples 1 and 2 and of Comparative Examples 1 and 2, and tested in accordance with the method described above. Comparative Example 1 here corresponds to the bag (10) with one web (1) of DuPont Tyvek® 1073B and one web (2) of HDPE, and Comparative Example 2 here corresponds to a bag (10) with one web (1) made of a polypropylene microfibre nonwoven (88-98 g/m²) and one web (2) of a laminate made of a polyester film (12 µm) and a polypropylene film (38 µm). TABLE 2 collates the results.

TABLE 2

| | Puncture resistance [N] | |
| Sample | Web 1 | Web 2 |
| --- | --- | --- |
| Example 1 | 16.9 N | 7.3 N |
| Example 2 | 16.9 N | 7.2 N |
| Comparative Example 1 | 16.9 N | 3.5 N |
| Comparative Example 2 | 16.0 N | 6.8 N |

The measured values reveal not only that with the layer structure of the invention the bag (10) permits improved detection of seal seam defects but also at the same time that the robustness of the packaging is further increased.

Remission $\tau_{vis}$

The respective seal seams and the two webs (1) and (2) of bags (10) of Examples 1 and 2 were tested in remission mode as described above. The sample of the webs (1, 2) here were taken at a lateral distance of 10 mm from the tested seal seam area. The results are shown in TABLE 3 below.

TABLE 3

| | | Remission $\tau_{VIS}$ [%] |
| --- | --- | --- |
| EXAMPLE 1 | Seal seam | 18.0 |
| | Web (1) | 77.1 |
| | Web (2) | 22.1 |
| EXAMPLE 2 | Seal seam | 18.0 |
| | Web (1) | 77.5 |
| | Web (2) | 22.0 |

Example 3

A bag (10) structure as in Example 1 was used for packaging, on an automated packing line, of vials (12) stored in a nest in a trough (14) protectively covered with a layer (16) of Tyvek® 1073 B. The protectively covered trough (14) here was placed into two enclosing bags (10, 10') as packaging as shown in FIG. 1. Sealing of the bags (10, 10') here was monitored by the installed camera-inspection system in transmitted light, viewing the Tyvek® side. Here again, the seal seams were extremely easy to detect, and defects could be discerned in a fully satisfactory manner.

What is claimed is:

1. Packaging for the sterile packaging of objects for medical, pharmaceutical or cosmetic applications, comprising:
   a first web;
   a second web; and
   a seal seam bonding the first and second webs to one another to define a portion of a bag, the bag having an internal side and an external side,
   the first web consists of a selectively permeable nonwoven fabric,
   the second web consists of a laminated film with a first layer, a second layer, and a third layer, the first layer is a polymer film arranged on the external side, the second layer is a lamination adhesive, and the third layer is another polymer film arranged on the internal side, the first layer having a melting point that is above a sealing-initiation temperature of the third layer by at least 20° C.,
   at least one of the first, second, and third layers comprising a pigment,
   wherein the seal seam, in an 8-bit greyscale image recorded in transmitted light and contrast-standardized, is within a greyscale value range of 50-200, and wherein the seal seam has a remission $\tau_{vis}$, measured in accordance with DIN 5033-1:2009-5 in remission mode with 2° observer, that is 10%-40%.

2. The packaging according to claim 1, wherein the polymer film of the first layer is a polyester film or polyamide film, and wherein the polymer film of the third layer is made of a material selected from a group consisting of polyethylene homopolymers, polyethylene copolymers, polypropylene homopolymers, polypropylene copolymers, polyester homopolymers, and polyester copolymers.

3. The packaging according to claim 1, wherein the selectively permeable nonwoven fabric is a microfibre nonwoven fabric made of a material selected from a group consisting of high-density polyethylene (HDPE), polypropylene (PP), and polyethylene terephthalate (PET).

4. The packaging according to claim 1, wherein the polymer film of the third layer is made of a material selected from a group consisting of high-density polyethylene (HDPE), medium-density polyethylene (MDPE), low-density polyethylene (LDPE), and linear low-density polyethylene (LLDPE).

5. The packaging according to claim 1, wherein the polymer film of the first layer is a polyester film or a polyamide film that is free from the pigment.

6. The packaging according to claim 1, the polymer film of the first layer is a polyethylene terephthalate (PET) or polybutylene terephthalate (PBT).

7. The packaging according to claim 1, wherein the seal seam exhibits greyscale values which are at least 30 units above greyscale values of a region surrounding the seal seam.

8. The packaging according to claim 1, wherein the portion of the bag defined by the seal seam comprises a closure of a filled bag.

9. The packaging of claim 8, further comprising a sealing or adhesive bonding connecting the first and second webs to one another to define remaining portions of the bag.

10. The packaging according to claim 1, wherein the seal seam exhibits a homogenous colour.

11. The packaging according to claim 1, wherein the seal seam has a strength that is at least 20 N/15 mm measured in accordance with DIN EN 868-5:2009 Annex D.

12. The packaging according to claim 1, wherein the first web has a puncture resistance measured in accordance with DIN EN 14477:2004 at test velocity 100 mm/min and with 0.8 mm tip diameter that is at least 10 N and/or wherein the second web has a puncture resistance measured in accordance with DIN EN 14477:2004 at test velocity 100 mm/min and with 0.8 mm tip diameter that is at least 4.5 N.

13. The packaging according to claim 1, further comprising another bag surrounding the bag.

14. The packaging according to claim 1, wherein the remission $\tau_{vis}$ of the seal seam exhibits a difference of 30-75 percentage points to a remission $\tau_{vis}$ of the first web measured in accordance with DIN 5033-1:2009-5 in remission mode with 2° observer.

15. The packaging according to claim 1, further comprising a tub or tray arranged in the bag.

16. The packaging according to claim 15, further comprising one or more objects for medical, pharmaceutical or cosmetic applications in the tub or tray.

17. The packaging according to claim 15, wherein the tub or tray comprises a protective covering of another selectively permeable nonwoven fabric sealed or adhesive bonded thereto.

* * * * *